US009012517B2

(12) United States Patent
Guillen et al.

(10) Patent No.: US 9,012,517 B2
(45) Date of Patent: Apr. 21, 2015

(54) POLYSACCHARIDE AND PROTEIN-POLYSACCHARIDE CROSS-LINKED HYDROGELS FOR SOFT TISSUE AUGMENTATION

(71) Applicant: Allergan, Inc., Irvine, CA (US)

(72) Inventors: Karina Heredia Guillen, Santa Barbara, CA (US); Ahmet Tezel, Fort Worth, TX (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/219,652

(22) Filed: Mar. 19, 2014

(65) Prior Publication Data

US 2014/0206774 A1    Jul. 24, 2014

Related U.S. Application Data

(62) Division of application No. 13/052,690, filed on Mar. 21, 2011, now Pat. No. 8,691,279.

(60) Provisional application No. 61/316,283, filed on Mar. 22, 2010.

(51) Int. Cl.
| *A61K 47/00* | (2006.01) |
| *A01N 25/00* | (2006.01) |
| *A61K 47/36* | (2006.01) |
| *A61L 27/20* | (2006.01) |
| *A61L 27/52* | (2006.01) |
| *A61K 47/42* | (2006.01) |

(52) U.S. Cl.
CPC ............... *A61K 47/36* (2013.01); *A61L 27/20* (2013.01); *A61L 27/52* (2013.01); *A61K 47/42* (2013.01)

(58) Field of Classification Search
None
See application file for complete search history.

(56) References Cited

U.S. PATENT DOCUMENTS

| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannnas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs et al. |
| 4,642,117 A | 2/1987 | Nguyen et al. |
| 4,713,448 A | 12/1987 | Balazs |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,980,930 A | 11/1999 | Fenton et al. |

(Continued)

FOREIGN PATENT DOCUMENTS

| CA | 949965 | 6/1974 |
| EP | 0273823 A1 | 7/1988 |

(Continued)

OTHER PUBLICATIONS

Aesthetic Buyers Guide, "Juvéderm Raises Standards"; Jan./Feb. 2007 (5 pp.), www.miinews.com.

(Continued)

*Primary Examiner* — Suzanne Ziska

(74) *Attorney, Agent, or Firm* — Barbara C. Potts; Linda A. Fox

(57) ABSTRACT

Disclosed herein are cohesive soft tissue fillers, for example, dermal and subdermal fillers, based on hyaluronic acids and optionally including proteins. In one aspect, hyaluronic acid-based compositions described herein include zero-length cross-linked moieties and optionally at least one active agent. The present hyaluronic acid-based compositions have enhanced flow characteristics, hardness, and persistence compared to known hyaluronic acid-based compositions. Methods and processes of preparing such hyaluronic acid-based compositions are also provided.

19 Claims, 3 Drawing Sheets

(56) References Cited

U.S. PATENT DOCUMENTS

| | | |
|---|---|---|
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg |
| 7,196,180 B2 | 3/2007 | Aeschlimann |
| 7,314,636 B2 | 1/2008 | Caseres et al. |
| 7,465,766 B2 * | 12/2008 | Calabro et al. ............... 525/54.1 |
| 7,491,709 B2 | 2/2009 | Carey |
| 7,741,476 B2 | 6/2010 | Lebreton |
| 7,902,171 B2 | 3/2011 | Reinmuller et al. |
| 8,124,120 B2 | 2/2012 | Sadozai |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons et al. |
| 2008/0274946 A1 | 11/2008 | Gimpapa |
| 2008/0279806 A1 | 11/2008 | Cho |
| 2008/0293637 A1 | 11/2008 | Schroeder et al. |
| 2009/0018102 A1 | 1/2009 | Moutet |
| 2009/0022808 A1 | 1/2009 | Champion |
| 2009/0028817 A1 | 1/2009 | Niklason et al. |
| 2009/0036403 A1 | 2/2009 | Stroumpolis |
| 2009/0042834 A1 | 2/2009 | Karageozian et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel et al. |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0263447 A1 * | 10/2009 | Asius et al. .................. 424/423 |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0316683 A1 | 12/2010 | Piron |
| 2011/0034684 A1 | 2/2011 | Yokokawa |
| 2011/0077737 A1 | 3/2011 | Stroumpoulis et al. |
| 2011/0118206 A1 | 5/2011 | Lebreton |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0224164 A1 | 9/2011 | Lebreton |
| 2012/0010146 A1 * | 1/2012 | Han et al. .................... 514/17.2 |
| 2012/0034462 A1 | 2/2012 | Stroumpoulis et al. |
| 2012/0071437 A1 | 3/2012 | Stroumpoulis et al. |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2012/0295870 A1 | 11/2012 | Lebreton |

FOREIGN PATENT DOCUMENTS

| | | | |
|---|---|---|---|
| EP | 0416250 | A2 | 3/1991 |
| EP | 0416846 | A2 | 3/1991 |
| EP | 1247522 | A1 | 10/2002 |
| EP | 1398131 | A1 | 3/2004 |
| EP | 1419792 | A1 | 5/2004 |
| EP | 1532991 | | 5/2005 |
| EP | 1726299 | A2 | 11/2006 |
| EP | 2236523 | | 10/2010 |
| FR | 2733427 | A1 | 10/1996 |
| FR | 2920000 | A1 | 2/2009 |
| FR | 2924615 | A1 | 6/2009 |
| JP | 55153711 | | 11/1980 |

(56) References Cited

FOREIGN PATENT DOCUMENTS

| | | |
|---|---|---|
| JP | 2007063177 | 3/2007 |
| WO | 8600079 | 1/1986 |
| WO | 8600912 | 2/1986 |
| WO | 9200105 | 1/1992 |
| WO | 9220349 | 11/1992 |
| WO | 9401468 | 1/1994 |
| WO | 9402517 | 2/1994 |
| WO | 9633751 | 4/1996 |
| WO | 9704012 | 2/1997 |
| WO | 9835639 | 8/1998 |
| WO | 9835640 | 8/1998 |
| WO | 0001428 | 1/2000 |
| WO | 0179342 | 10/2001 |
| WO | 0205753 | 1/2002 |
| WO | 0206350 | 1/2002 |
| WO | 0209792 | 2/2002 |
| WO | 0217713 | 3/2002 |
| WO | 03007782 | 1/2003 |
| WO | 2004020473 | 3/2004 |
| WO | 2004022603 | 3/2004 |
| WO | 2004073759 | 9/2004 |
| WO | 2004092223 | 10/2004 |
| WO | 2005040224 | 5/2005 |
| WO | 2005067944 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | 2007136738 | 11/2007 |
| WO | WO 2007/128923 | 11/2007 |
| WO | WO 2008/034176 | 3/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | 2009-026158 A2 | 2/2009 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | 2010-053918 A1 | 5/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |

OTHER PUBLICATIONS

Adams; "An Analysis of Clinical Studies of the Uses of Crosslinked Hyaluronan, Hylan, in the Treatment of Osteoarthritis"; J. Rheumatol Suppl.; vol. 39; pp. 16-18; Aug. 1993.

Albano et al.; "Hyroxyethyl Radicals in Ethanol Hepatotoxicity"; Frontiers in Bioscience; vol. 4; pp. 533-540; 1999.

Allemann et al.; "Hyaluronic acid gel (JUVADERM) preparations in the treatment of facial wrinkles and folds"; Clinical Interventions in Aging; vol. 3, No. 4; pp. 629-634; 2008.

Antunes et al.; "Efficacy of Intrarectal Lidocaine Hydrochloride Gel for Pain control in Patients Undergoing Transrectal Prostate Biopsy"; International Braz J Urol; vol. 30, No. 5; pp. 380-383; Sep.-Oct. 2004.

Atanassoff et al.; "The Effect of Intradermal Administration of Lidocaine and Morphine on the Response to Thermal Stimulation"; Anesth Analg; vol. 84; pp. 1340-1343; 1997.

Baumann et al.; "Comparison of smooth-gel hyaluronic acid dermal fillers with cross-linked bovine collagen: a multicenter, double-masked, randomized, within-subject study"; Dermatol. Surg.; vol. 33(Suppl 2); pp. S128-S135 2007.

Beasley et al.; "Hyaluronic acid fillers: a comprehensive review"; Facial Plast. Surg.; vol. 25, No. 2; pp. 86-94; 2009.

Beer; "Dermal fillers and combinations of fillers for facial rejuvenation"; Dermatol. Clin.; vol. 27, No. 4; pp. 427-432; 2009.

Belda et al.; "Hyaluronic acid combined with mannitol to improve protection against free-radical endothelial damage: Experimental Model"; J.Cataract Refract Surg; Vo. 31; pp. 1213-1218; 2005.

Bircher, et al.; "Delayed-Type Hypersensitivity to Subcutaneous Lidocaine With Tolerance to Articaine: Confirmation by In Vivo and In Vitro Tests"; Contact Dermatitis; vol. 34; pp. 387-389; 1996.

Bluel et al.; "Evaluation of Reconstituted Collagen Tape as a Model for Chemically Modified Soft Tissues", Biomat. Med. Dev. Art. Org.; vol. 9(1); pp. 37-46; 1981.

Capozzi et al., "Distant Migration of Silicone Gel From a Ruptured Breast Implant", Plastic and Reconstructive Surgery; vol. 62; pp. 302-303; 1978.

Carlin et al., "Effect of anti-inflammatory drugs on xanthine oxidase and xanthine oxidase induced depolymerization of hyaluronic acid"; Agents and Actions; vol. 16 (5); pp. 377-384; 1985.

Carruthers et al.; "The science and art of dermal fillers for soft-tissue augmentation"; J. Drugs Dermatol; vol. 8(4); pp. 335-350; 2009.

Champion et al., "Role of Target Geometry in Phagocytosis"; S. Proc. Nat. Acad. Sci.; vol. 103; No. 13; pp. 4930-4934; Mar. 28, 2006.

Chin et al., "Allergic Hypersensitivity to Lidocaine Hydrochloride", International journal of Dermatology, vol. 19; pp. 147-148; Apr. 1980.

Chvapil, "Collagen Sponge: Theory and Practice of Medical Applications", J. Biomed Mater. Res., vol. II, pp. 721-741; 1977.

Clark et al., "The Influence of Triamcinolone Acetonide on Joint Stiffness in the Rat", J Bone Joint Surg; vol. 53-A; pp. 1409-1414; Oct. 1971.

Cohen et al., "Organization and Adhesive Properties of the Hyaluronan Pericellular Coat of Chrondrocytes and Epithelial Cells", Biophys J.; vol. 85; pp. 1996-2005; Sep. 2003.

Deland, "Intrathecal Toxicity Studies with Benzyl Alcohol", Toxicol Appl Pharmacol; vol. 25; pp. 153-156; 1973.

Desai et al., J Pharm Sci Abstract only; 84 (2): 212-215; Feb. 1995.

Eyre et al., Top Curr. Chem., vol. 247, pp. 207-229; 2005.

Falcone et al.; "Crosslinked hyaluronic acid dermal fillers: a comparison of rheological properties." J Biomed Mater Res; vol. 87(1); pp. 264-271; 2008.

Falcone et al.; "Temporary polysaccharide dermal fillers: a model for persistence based on physical properties." Dermatol Surg.; vol. 35(8); pp. 1238-1243; 2009.

Farley et al., "Diluting Lidocaine and Mepivacaine in Balanced Salt Solution Reduces the Pain of Intradermal Injection", Regional Anesthesia; vol. 19(1); pp. 48-51; 1994.

Frati et al., "Degradation of hyaluronic acid by photosensitized riboflavin in vitro. Modulation of the effect by transition metals, radical quenchers, and metal chelators"; Free Radical Biology Medicine; vol. 22 (7); pp. 1139-1144 1997.

Fujinaga et al., "Reproductive and Teratogenic Effects of Lidocaine in Sprague-Dawley Rats"; Anesthesiology vol. 65; pp. 626-632; 1986.

Gammaitoni et al., "Pharmacokinetics and safety of continuously applied lidocaine patches 5%", Am J Health Syst Pharm; vol. 59; pp. 2215-2220; Nov. 15, 2002.

GinShiCel MH Hydroxy Propyl methyl Cellulose, Web Page http://www.ginshicel.cn/MHPC.html, Nov. 12, 2008.

Gold; "Use of Hyaluronic acid fillers for the treatment of the aging face"; Clin. Interventions Aging; vol. 2(3); pp. 369-376; 2007.

Goldberg; "Breakthroughs in US dermal fillers for facial soft-tissue augmentation"; J Cosmet Laser Ther; vol. 11; pp. 240-247; 2009.

Graefe et al., "Sensitive and specific photometric determination of mannitol in human serum"; Clin Chem Lab Med; vol. 41, No. 8; pp. 1049-1055; 2003.

(56) References Cited

OTHER PUBLICATIONS

Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.
Grillo et al., "Thermal Reconstitution of Collagen from Solution and the Response to Its Heterologous Implantation", JSR; vol. II, No. 1, pp. 69-82; Jan. 1962.
Hassan et al., "Effects of Adjuvants to local anaesthetics on their duration. III. Experimental studies of hyaluronic acid"; Abstract Pub Med [Acta Anesthesiol Scand; vol. 29(4); pp. 384-388; May 1985.
Hayashibara, "AA2G"; Sep. 23, 2007, http://web.archive.org/web/2007923072010/http://www.hayashibara-intl.com/cosmetics/aa2g.html.
Helliwell, "Use of an Objective Measure of Articular Stiffness to Record Changes in Finger Joints After Intra-Articular Injection of Corticosteroid", An Theum Dis; vol. 56; pp. 71-73; 1997.
Hertzberger-Ten Cate et al., "Intra-Articular Steroids in Pauciarticular Juvenile Chronic Arthritis", Type I, Eur J Pediatr; vol. 150; pp. 170-172; 1991.
Hetherington, "Potential for Patient Harm From Intrathecal Administration of Preserved Solutions", Abstract only Med J; vol. 173(3); p. 141; Aug. 2000.
Hurst, "Adhesive Arachnoiditis and Vascular Blockage Caused by Detergents and Other Chemical Irritants: an Experimental Study", J Path Bact, vol. LXX, No. 70; pp. 167-177; 1955.
Intramed Mannitol 20% m/v Infusion, package insert, pp. 1-2 (2010) http://home.intekom.com/pharm/intramed/manitl20.html.
Jones et al., "Intra-Articular Hyaluronic Acid Compared to Intra-Articular Triamcinolone Hexacetonide in Inflammatory Knee Osteoarthritis", Osteoarthritis Cartilage, vol. 3; pp. 269-273; 1995.
Kablik et al. "Comparative physical properties of hyaluronic acid dermal fillers." Dermatol. Surg.; vol. 35(Suppl. 1); pp. 302-312; 2009.
Klein, "Skin Filling Collagen and Other Injectables of the Skin", Dermatologic Clinics; vol. 19, No. 3, pp. 491-588; Jul. 2001.
Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.
Kulicke et al., "Visco-Elastic Properties of Sodium Hyaluronate Solutions," American Institue of Physics; 3 pages; 2008.
Laeschke, "Biocompatibility of Microparticles into Soft Tissue Fillers", Semin. Cutan. Med. Surg., vol. 23; pp. 214-217; 2004.
Lamar et al., "Antifibrosis Effect of Novel Gels in Anterior Ciliary Slerotomy (ACS)," ARVO 2002 abstract only.
Levy et al., "Lidocaine hypersensitivity after subconjunctival injection", Can J Ophthalmol 2006; vol. 41, No. 2; pp. 204-206.
Lupo; "Hyaluronic acid fillers in facial rejuvenation." Semin. Cutan. Med. Surg.; vol. 25; pp. 122-126; 2006.
Mackley et al., "Delayed-Type Hypersensitivity to Lidocaine", Arch Dermatol, vol. 139; pp. 343-346; Mar. 2003.
Mancinelli et al., "Intramuscular High-Dose Triamcinolone Acetonide in the Treatment of Severe Chronic Asthma", West J. Med; vol. 167(5); pp. 322-329; Nov. 1997.
Matsumoto et al., "Reducing the Discomfort of Lidocaine Administration through pH Buffering," Journal of Vascular and Interventional Radiology; vol. 5, No. 1; pp. 171-175; Nov. 1997.
McCarty et al., "Inflammatory Reaction After Intrasynovial Injection of Microcrystalline Adrenocorticosteroid Esters", Arthritis and Rheuymatism; vol. 7(4); pp. 359-367; 1964.
McCleland et al.; "Evlaution of Artecoll Polymethacrylate Implant for Soft-Tissue Augmentation: Biocompatibility and Chemical Chartacterization"; Plastric Reconstructive Surgery; vol. 100(6); pp. 1466-1474; Nov. 1997.
McPherson et al; "Development and Biochemical Characterization of Injectable Collagen," J. Dermatol Surg Oncol; vol. 14 (Suppl1); pp. 13-20; Jul. 7, 1988.

Orvisky et al., "High-molecular-weight hyaluronan—a valuable tool in testing the antioxidative activity of amphiphilic drugs stobadine and vinpocetine"; J. Pharm. Biomed. Anal.; vol. 16; pp. 419-424; 1997.
Osmitrol (generic name Mannitol),Official FDA Information, side effects and uses, pp. 1-10 (2010) http://www.drugs.com/pro/osmitrol.html.
Prestwich; "Evaluating drug efficacy and toxicology in three dimensions: using synthetic extracellular matrices in drug discovery"; Accounts of Chemical Research; vol. 41, No. 1; pp. 139-148; Jan. 2008.
Rehakova et al.; "Properties of collagen and hyaluronic acid composite materials and their modifications by chemical crosslinking," Journal of Biomedical Materials Research; vol. 30; pp. 369-372; 1996.
Remington's Pharmaceutical Science Mac Publishing Company, Easton, PA 16th Edition 1980; 1- page.
Rosenblatt et al., "The Effect of Collagen Fiber Size Distribution on the Release Rate of Proteins from Collagen Matrices by Diffusion", J. Controlled Rel., vol. 9; pp. 195-203; 1989.
Rosenblatt et al., "Chain Rigidity and Diffusional Release in Biopolymer Gels", Proceed. Inter. Symp. Control. Rel. Bioact. Mater.; vol. 20; pp. 264-265; 1993; Controlled Release Society, Inc.
Sannino et al., "Crosslinking of Cellulose Derivatives and Hyaluronic Acid with Water-Soluble Carbodiimide," Polymer; vol. 46; pp. 11206-11212 ; 2005.
Sculptra® Aesthetic (injectable poly-L-lactic acid) Directions for Use, Dermik Laboratories product insert (Jul. 2009), sanofi-aventis U.S. LLC; 10 pages.
Segura et al. "Crosslinked hyaluronic acid hydrogels: a strategy to functionalize and pattern." Biomaterials; vol. 26; pp. 359-371; 2005.
Selvi et al, "Arthritis Induced by Corticosteroid Crystals", J. Rheumatology; vol. 34:3; 1 page; 2004.
Serban et al., "Modular Extracellular Matrices: Solutions for the Puzzle"; Methods; vol. 45(1)pp. 93-98; 2008.
Shu et al., "Synthesis and evaluation of injectable, in situ crosslinkable synthetic extracellular matrices for tissue engineering"; J. Biomed. Mater. Res. A.; vol. 79(4); pp. 902-912; 2006.
Silver et al., "Physical Properties of Hyaluronic Acid and Hydroxypropylmethylcellulose in Solution: Evaluation of Coating Ability"; Journal of Applied Biomaterials; vol. 5; pp. 89-98; 1994.
Smith et al., "Five Percent Lidocaine Cream Applied Simultaneously to Skin and Mucosa of the Lips Creates Excellent Anesthesia for Filler Injections", Dermatol Surg; vol. 31; pp. 1635-1637; 2005.
Tezel et al.,, "The science of hyaluronic acid dermal fillers", J. Cosmet. Laser Ther.; vol. 10; pp. 35-42; 2008.
TRB Chemedica Ophthalmic Line, VISIOL, product info., pp. 1-2; No date.
VISIOL, Viscoelstic gel for use in ocular surgery, (2010) p. 1, htt://www.trbchemedica.com/index.php/option=com_content&tas.
Waraszkiewicz et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, pp. 1215-1218, Nov. 1981.
Xia et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al., "Effect of Cross-Linking Reagents for Hyaluronic Acid Hydrogel Dermal Fillers on Tissue Augmentation and Regeneration", Bioconjugate Chem., vol. 21; pp. 240-247; 2010.
Yui, et al., "Inflammation responsive degradation of crosslinked hyaluronic acid gels," Journal of Controlled Release, vol. 22; pp. 105-116; 1992.
Yui et al., "Photo-responsive degradation of heterogeneous hydrogels comprising crosslinked hyaluronic acid and lipid microspheres for temporal drug delivery," Journal of Controlled Release; vol. 26; pp. 141-145; 1993.
Yun et al., "Hyaluronan Microspheres for Sustained Gene Delivery and Site-Specific Targeting", Biomaterials, vol. 25, pp. 147-157, 2004.

(56) References Cited

OTHER PUBLICATIONS

Zheng Shu et al., "In situ crosslinkable hyaluronan hydrogels for tissue engineering." Biomaterials; vol. 25; pp. 1339-1348; 2004.

Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Lindvall et al.; "Influcence of Various Compounds on the Degradation of Hyaluronic Acid by a Myeloperoxidase System"; Chemcio-Biological Interactions; vol. 90; pp. 1-12; 1994.

Weidmann; "New Hyaluronic Acid Filler for Subdermal and Long-Lasting Volume Restoration of the Face"; European Dermatology; pp. 65-68; 2009.

Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

Buck et al, "Injectable Fillers for our Facial Rejuvenation: a Review", Journal of Plastic, Reconstructive and Aesthetic Surgery, (2009), 62:11-18, XP002668828.

Park et al., "Biological Characterization of EDC-crosslinked Collagen-Hyaluronic Acid Matrix in Dermal Tissue Restoration", Biomaterials 24 (2003) 1631-1641.

Park et al., "Characerization of Prous Collagen/Hyaluronic Acid Scaffold Modified by 1-ethyl-3-(3-dimethylaminopropyl) carbodiimide cross-linking", Biomaterials 23 (2002): 1205-1212.

Helary et al., "Concentrated collagen hydrogels as dermal substitutes", Biomaterials 31 (2010) 481-490.

Millay et al.; "Vasoconstrictors in Facial Plastic Surgery"; Archives of Otolaryngology—Head & Neck Surgery; vol. 117; pp. 160-163; Feb. 1991.

Wahl, "European Evaluation of a New Hyaluronic Acid Filler Incorporating Lidocaine", Journal of Cosmetic Dermatology; vol. 7; pp. 298-303; 2008.

\* cited by examiner

POLYSACCHARIDE AND PROTEIN-POLYSACCHARIDE CROSS-LINKED HYDROGELS FOR SOFT TISSUE AUGMENTATION

RELATED APPLICATION

This application is a divisional of U.S. patent application Ser. No. 13/052,690, filed Mar. 21, 2011, which claims priority to U.S. Provisional Patent Application No. 61/316,283, filed on Mar. 22, 2010, the entire disclosure of each of these application being incorporated herein by this reference.

BACKGROUND

Various injectable dermal filler products have been developed for treating or correcting facial imperfections, for example, wrinkles and volume loss due to the natural effects of aging. Injectable "dermal fillers" temporarily restore a smoother, more youthful appearance.

Ideally, dermal fillers are long-lasting, soft, smooth and natural appearing when introduced into or beneath the skin. Further, these products are preferably easy to introduce into a patient using a fine gauge needle and a low extrusion force such that there will be minimal discomfort to the patient.

Collagen based soft tissue fillers were developed over 20 years ago, and for some time, bovine collagen-based fillers were the only U.S. Food and Drug Administration (FDA)-approved dermal fillers. Because these early dermal fillers were bovine-based, one of the main disadvantages to their use has been the potential for allergic reaction in patients.

In February 2003, human-derived collagen filler compositions received FDA approval. These collagens provide the advantage of a significantly reduced risk of allergic reactions. Unfortunately, such human-derived collagen filler compositions tended to rapidly degrade shortly after injection.

In December 2003, the first hyaluronic acid (HA)-based dermal filler dermal filler was approved by the FDA. This was rapidly followed by the development of many other HA-based dermal fillers.

HA, also known as hyaluronan, is a naturally occurring, water soluble polysaccharide, specifically a glycosaminoglycan, which is a major component of the extra-cellular matrix and is widely distributed in animal tissues. HA has excellent biocompatibility and does not cause allergic reactions when implanted into a patient. In addition, HA has the ability to bind to large amounts of water, making it an excellent volumizer of soft tissues.

The development of HA-based fillers which exhibit ideal in vivo properties as well as ideal surgical usability has proven difficult. For example, HA-based fillers that exhibit desirable stability properties in vivo, can be so highly viscous that injection through fine gauge needles is difficult. Conversely, HA-based fillers that are relatively easily injected through fine gauge needles often have relatively inferior stability properties in vivo.

Current hydrogel synthesis strategies perform cross-linking of HA under basic conditions using small molecules to link the respective chains together. However, under these conditions the HA chains hydrolyze into shorter fragments and small molecule linkers are introduced into the hydrogel. It is an objective of the present invention to provide stable, elastic soft tissue fillers with improved rheological properties.

SUMMARY

The present invention relates to soft tissue fillers, for example, dermal and subdermal filler compositions, hereinafter, sometimes, interchangeably referred to as "dermal fillers", "soft tissue fillers" or "fillers".

In one aspect of the invention, a composition is provided which is a hydrogel comprising a cross-linked biocompatible polymer having zero-length cross-linked moieties. In some embodiments, the composition further comprises at least one other active ingredient incorporated into the cross-linked biocompatible polymer.

The hydrogel may be formed by reacting at least one cross-linkable biocompatible polymer with at least one zero-length cross-linking agent at neutral pH. For example, the neutral pH can be between about 6.0 and about 8.0, such as for example, between about 6.5 and about 7.5, such as for example about 7.0.

In some embodiments, the cross-linkable biocompatible polymer is hyaluronic acid (HA) and the zero-length cross-linking agent is 1-ethyl-3-(3-dimethylaminopropyl) carbodiimide (EDC).

In some embodiments, the zero-length cross-linking agent is reacted with the HA in the presence of N-hydroxysuccinimide (NHS), sulfo-NHS (or sulfonyl-NHS) or 4-dimethylaminopyridine (DMAP).

In some embodiments, the hydrogel further includes at least one second cross-linked biocompatible polymer. The second cross-linked biocompatible polymer can be, for example, a protein such as elastin.

In some embodiments, the hydrogel can include an active agent selected from the group consisting of enzyme inhibitors, anesthetic agents, medicinal neurotoxins, antioxidants, anti-infective agents, anti-inflammatory agents, ultraviolet (UV) light blocking agents, dyes, hormones, immunosuppressants, and combinations thereof.

The present invention further provides a method for making a hydrogel for soft tissue augmentation. The method includes providing at least one cross-linkable biocompatible polymer; dissolving the at least one cross-linkable biocompatible polymer in a buffered solution wherein the buffered solution maintains a pH from approximately 6.0 to approximately 8.0; adding at least one zero-length cross-linking agent to the buffered solution to form a reaction mixture; and allowing the reaction mixture to stand for a time appropriate to form a hydrogel suitable for soft tissue augmentation.

Embodiments of the method of the invention can include one or more of the following features. The at least one cross-linkable biocompatible polymer can be HA. The buffered solution can be a phosphate buffered saline having a pH of between about 6.5 and about 7.5. The at least one zero-length cross-linking agent can be EDC.

In some embodiments, NHS is included in the adding step.

In some embodiments, the method includes a dialyzing step after the adding step.

In some embodiments, the method includes at least one second cross-linkable biocompatible polymer. The second cross-linked biocompatible polymer can be, for example, a protein such as elastin.

In one aspect of the invention, the method includes adding an active agent. The active agent may be an active agent selected from the group consisting of enzyme inhibitors, anesthetic agents, medicinal neurotoxins, antioxidants, anti-infective agents, anti-inflammatory agents, ultraviolet light blocking agents, dyes, hormones, immunosuppressants, and combinations thereof.

In a specific embodiment of the invention, a method for making a hydrogel for soft tissue augmentation is provided which comprises the steps of providing a 0.1 M phosphate buffered saline (PBS) solution having a pH between approximately 6.5 and approximately 7.5; dissolving from about 20 to about 80 mg/mL HA from about 2 to about 20 weight percent soluble elastin in the PBS to form a polymer mixture; adding about 5 to about 30 mol percent EDC and NHS to the polymer mixture to form a reaction mixture; allowing the reaction mixture to react for about 12 to about 48 hours at about 22° to about 60° C. to form a gel; dialyzing the gel against PBS to form a purified gel; and sizing the purified gel to form a hydrogel for soft tissue augmentation. In some embodiments, the method includes adding an active agent selected from the group consisting of enzyme inhibitors, anesthetic agents, medicinal neurotoxins, antioxidants, anti-infective agents, anti-inflammatory agents, ultraviolet light blocking agents, dyes, hormones, immunosuppressants, and combinations thereof.

DETAILED DESCRIPTION

Figure 1:
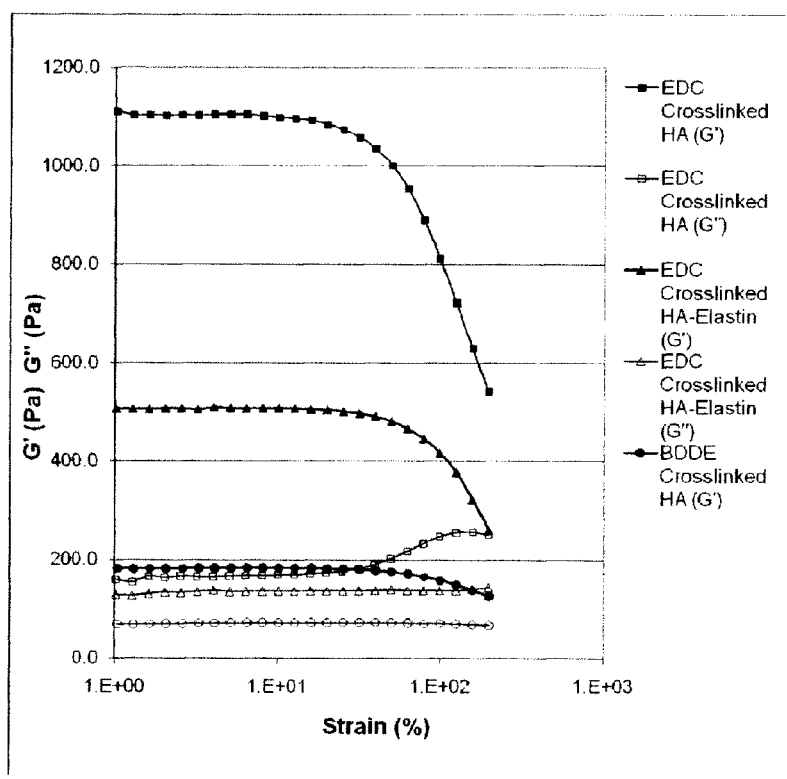
FIG. 1 graphically illustrates the elasticity and viscosity of EDC/NHS cross-linked HA and HA-elastin in accordance with an embodiment of the invention.

Where the definition of terms as used in the specification departs from the commonly used meaning of the term, applicant intends to utilize the definitions provided herein, unless specifically indicated.

The present description generally relates to soft tissue fillers, for example, dermal and subdermal fillers, based on cross-linked biocompatible polymers. In one aspect, the compositions described herein include hydrogels comprising at least one cross-linked biocompatible polymer having zero-length cross-linked moieties and optionally at least one other active ingredient incorporated into the cross-linked biocompatible polymer. The present compositions, which include HA-based hydrogels, have enhanced rheology (i.e., flow characteristics), elasticity, and persistence relative to known HA-based hydrogels. Methods or processes of preparing such compositions are also provided, as well as products made by such methods or processes.

A surprising advantage of the compositions and methods of the present description is that the molecular weight of the polymer chains, such as HA, remains high and the resultant hydrogels have improved rheological properties while at the same time have low extrusion forces. Hydrogels with fine-tuned hardness and elasticity are beneficial for the development of biomaterials suitable for soft tissue augmentation.

In various embodiments, hydrogels of the present description include HA as a biocompatible polymer and are therefore HA-based. HA-based as used herein refers to compositions including cross-linked HA and compositions including cross-linked HA plus one or more other cross-linked polymers. In addition, HA can refer to hyaluronic acid and any of its hyaluronate salts, including, but is not limited to, sodium hyaluronate (NaHA), potassium hyaluronate, magnesium hyaluronate, calcium hyaluronate, and combinations thereof. The use of more than one biocompatible polymer is specifically not excluded from the present description. Hydrogels of the present description can include more than one biocompatible polymer, such as, for example, 2, 3, 4, 5, 6, 7, 8, 9, 10, or more biocompatible polymers. Suitable biocompatible polymers include polysaccharides (e.g., HA, chitosan, chondroitin sulfate, alginate, carboxymethylcellulose), poly(ethyleneglycol), poly(lactic acid), poly(hydroxyethylmethacrylate), poly(methylmethacrylate), proteins (e.g., elastin and collagen).

Generally, the HA concentration in the compositions described herein is preferably at least 10 mg/mL and up to about 100 mg/mL. For example, the concentration of HA in some of the compositions is in a range between about 15 mg/mL and about 80 mg/mL, or about 15 mg/mL to about 30 mg/mL. In some embodiments, the concentration of HA is about 26 mg/mL. In some embodiments, hydrogels are formed by reacting at least one cross-linkable biocompatible polymer, such as HA and/or protein, with at least one zero-length cross-linking agent. Generally, zero-length cross-linking agents couple polymers without adding any additional spacer arm atoms and therefore zero-length cross-linking agents are not incorporated into the cross-linked polymer matrix. Suitable zero-length cross-linking agents include carbodiimides, such as, for example, 1-ethyl-3-(3-dimethylaminopropyl) carbodiimide (EDC). Non-water soluble carbodiimides include dicyclohexylcarbodiimide (DCC) and diisopropylcarbodiimide (DIC), which may also be suitable.

Carbodiimide-mediated coupling between carboxylates and alcohol or amine functional groups proceeds readily at ambient temperature, neutral pH and under aqueous conditions. Neutral pH can be, for example, between about 6.0 and about 8.0, such as between about 6.5 and about 7.5, such as about 7.0. Typically in water, 1-ethyl-3-(3-dimethylaminopropyl) carbodiimide hydrochloride (EDC) can be used to mediate esterification between carboxylates and alcohols or amidation between carboxylates and amines. Thus, cross-linked HA is formed by exploiting reactive groups present on HA (e.g, carboxylate and alcohol). In addition, by taking advantage of the high reactivity of amine groups on proteins, amidation between lysine side-chains of proteins with carboxylate groups of HA is achieved to form HA-protein cross-linked hydrogels. Cross-linking agents and unreacted polymers can be removed by dialysis.

In some embodiments, EDC is used in conjunction with N-hydroxysuccinimide (NHS) or sulfonyl-NHS (sulfo-NHS), collectively referred to as "NHS" herein. NHS stabilizes reactive intermediates formed by EDC; thus, the addition of NHS can increase the coupling efficiency of EDC. Alternatively, 4-dimethylaminopyridine (DMAP) can be used to catalyze the coupling reaction.

Without being limited thereto, the HA-based compositions in accordance with the present description include cross-linked HA-based compositions and at least partially cross-linked HA-based compositions. Uncross-linked HA as used herein refers to both truly uncross-linked (e.g., "free") HA chains as well as lightly cross-linked chains and fragments thereof that are generally in soluble liquid form.

The soft tissue fillers of the present description can include an active agent selected from the group consisting of enzyme inhibitors, anesthetic agents, medicinal neurotoxins (e.g., *botulinum* toxin and clostridium toxin), antioxidants, anti-infective agents (e.g., antibiotics), anti-inflammatory agents, ultraviolet (UV) light blocking agents, dyes, hormones, immunosuppressants, and combinations thereof.

In addition, the soft tissue fillers of the present invention can include one or more anesthetic agents in an amount effective to mitigate pain experienced upon injection of the composition. The local anesthetic can be selected from the group of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dycyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In one embodiment, the anesthetic agent is lidocaine, such as in the form of lidocaine HCl. The compositions described herein may have a lidocaine or other anesthetic in a concentration of between about 0.1% and about 5% by weight of the composition, for example, about 0.2% to about 1.0% by weight of the composition. In one embodiment, the composition has a lidocaine concentration of about 0.3% by weight (w/w %) of the composition. The concentration of lidocaine in the compositions described herein can be therapeutically effective meaning the concentration is adequate to provide a therapeutic benefit.

The present description also provides methods for making hydrogels. The methods can include providing at least one cross-linkable biocompatible polymer, such as HA. The initial step of providing raw HA material can be in the form of dry HA fibers or powder. The raw HA material may be HA, its salts and/or mixtures thereof. The HA material can comprise, for example, NaHA fibers or powder of bacterial-sourced NaHA. In some aspects of the present description, the HA material may be animal derived. The HA material may be a combination of raw materials including HA and at least one other polysaccharide, for example, glycosaminoglycan (GAG).

In some embodiments, the HA material in the compositions nearly entirely comprises or consists of high molecular weight HA. That is, nearly 100% of the HA material in the present compositions may be high molecular weight HA. In other embodiments, the HA material in the compositions comprises a combination of high molecular weight HA and low molecular weight HA.

The HA material of the compositions may comprise between about 5% to about 95% high molecular weight HA with the balance of the HA material including low molecular weight HA. In a typical composition according to the present description, the ratio of high molecular weight to low molecular weight HA is at least about, and preferably greater than 2 (w/w≥2) with the high molecular weight HA having a molecular weight of above about 1.0 MDa.

It will be appreciated by those of ordinary skill in the art that the selection of high and low molecular weight HA material and their relative percentages or ratios is dependent upon the desired characteristics, for example, extrusion force, elastic modulus, viscous modulus and persistence of the final HA-based product. For additional information that may be helpful in understanding this and other aspects of the present description, see U.S. Patent Application Publication No. 2006/0194758, the entire description of which is incorporated herein by this reference.

HA-based gels can be prepared according to the present description by first cleaning and purifying dry or raw HA material having a desired high/low molecular weight ratio. These steps generally involve hydrating the dry HA fibers or powder in the desired high/low molecular weight ratio, for example, using pure water, and filtering the material to remove large foreign matters and/or other impurities. The filtered, hydrated material is then dried and purified. The high and low molecular weight HA may be cleaned and purified separately, or may be mixed together, for example, in the desired ratio, just prior to cross-linking.

Methods of making hydrogels in accordance with the present description can include the step of dissolving the cross-linkable biocompatible polymer in a buffered solution. In some embodiments, the buffered solution is maintained at a pH between about 6.0 and about 8.0, such as between about 6.5 and about 7.5, such as at about 7.0. In a preferred embodiment, the biocompatible polymer is HA and the buffer is phosphate buffered saline (PBS). In some embodiments, a second biocompatible polymer is added. When more than one biocompatible polymer is used, the polymers can be added in ratios which yield suitable flow characteristics, elasticity, viscosity, and persistence. In a preferred embodiment, the second biocompatible polymer is a protein such as elastin. In a particularly preferred embodiment, about 20 to about 80 mg/mL HA is dissolved in the buffer solution, and about 2 to about 20 weight percent of soluble elastin is dissolved in the buffer solution.

The methods of making hydrogels in accordance with the present description can include the step of adding at least one zero-length cross-linking agent to the buffered solution. The use of more than one cross-linking agent or a different cross-linking agent is not excluded from the scope of the present description. In a preferred embodiment, the zero-length cross-linking agent is EDC. NHS can be added to the reaction mixture before, or together with EDC to increase cross-linking efficiency. EDC and NHS can be added in any ratio, such as 10:1, 5:1, 2:1, 1:1, 1:2, 1:5, and 1:10. In a preferred embodiment, EDC and NHS are added in one portion (i.e., 1:1 ratio). EDC and NHS can be prepared at any suitable concentration, such as between about 1 to about 50 mol percent, and more preferably between about 5 to about 30 mol percent.

The reaction mixture is allowed to stand for a time appropriate to form a hydrogel suitable for soft tissue implantation. In some embodiments, the time is from between about 12 hours to about 72 hours, such as between about 12 and about 48 hours, such as about 24 hours. In some embodiments, the reaction mixture is maintained at an appropriate temperature, such as between about 22 to about 60 degrees Celsius.

The step of cross-linking may be carried out using any means known to those of ordinary skill in the art. Those skilled in the art appreciate how to optimize conditions of cross-linking according to the nature of the biocompatible polymers, and how to carry out cross-linking to an optimized degree. A degree of cross-linking is preferably sufficient for the final hydrogel composition obtained from the present methods to remain implanted at the injection site without excessive diffusion away from the injection site. In some embodiments, the degree of cross-linking is at least about 2% to about 20%, and more preferably is about 4% to about 12%, wherein the degree of cross-linking is defined as the percent weight ratio of the cross-linking agent to HA-monomeric units in the composition. The degree of cross-linking can be less than about 6% or more preferably less than about 5%.

The method of making a hydrogel can include the step of dialyzing the hydrogel after the hydrogel is formed to remove cross-linking agents, unreacted starting materials, and by-products such as N-acylurea. In some embodiments, the dialysis is performed using a buffer solution. In a preferred embodiment, the buffer solution is PBS. The purified hydrogel can then be sized using any suitable method, such as by passing through a stainless steel screen having the desired mesh size.

The cross-linked, HA-based gels can comprise a cross-linked HA component capable of absorbing at least about one time its weight in water. When neutralized and swollen, the cross-linked HA component and water absorbed by the cross-linked HA component is in a weight ratio of about 1:1.

The compositions described herein display an elastic modulus and viscous modulus which is dependent on the specific biocompatible polymers used and the presence and/or absence of at least one active agent. In some embodiments, the elastic modulus of the HA-based compositions can be at least about 50 Pa, but is more preferably between about 150 Pa and about 1500 Pa, such as between about 500 Pa to about 1200 Pa. In some embodiments, the viscous modulus can be between about 50 Pa to about 500 Pa, such as between about 50 Pa to about 200 Pa. In one exemplary embodiment, the viscous modulus is about 160 Pa.

In some embodiments, the method includes the step of adding an active ingredient to the hydrogel. As discussed in more detail above, the active ingredient can be selected from the group consisting of enzyme inhibitors, anesthetic agents, medicinal neurotoxins, antioxidants, anti-infective agents, anti-inflammatory agents, ultraviolet light blocking agents, dyes, hormones, immunosuppressants, and combinations thereof. The use of more than one active agent is specifically not excluded from the present description. In some embodiments, one or more active agents are added to the purified hydrogel. In other embodiments, one or more active agents are added to the reaction buffer and are cross-linked with the biocompatible polymer and/or the active agents are entrapped or encased by the cross-linked biocompatible polymer.

Syringes useful for administering the hydrogels of the present description include any syringe known in the art capable of delivering viscous dermal filler compositions. The syringes generally have an internal volume of about 0.4 mL to about 3 mL, more preferably between about 0.5 mL and about 1.5 mL or between about 0.8 mL and about 2.5 mL. This internal volume is associated with an internal diameter of the syringe which affects the extrusion force needed to inject high viscosity dermal filler compositions. The internal diameters are generally about 4 mm to about 9 mm, more preferably from about 4.5 mm to about 6.5 mm or from about 4.5 mm to about 8.8 mm. Further, the extrusion force needed to deliver the HA-based compositions from the syringe is dependent on the needle gauge. The gauges of needles used generally include gauges between about 18 G and about 40 G, more preferably about 25 G to about 33 G or from about 16 G to about 25 G. A person of ordinary skill in the art can determine the correct syringe dimensions and needle gauge required to arrive at a particular extrusion force requirement.

The extrusion forces displayed by the HA-based compositions described herein using the needle dimensions described above are applied using injection speeds that are comfortable to a patient. Comfortable to a patient is used to define a rate of injection that does not injure or cause excess pain to a patient upon injection to the soft tissue. One skilled in the art will appreciate that comfortable as used herein includes not only patient comfort, but also comfort and ability of the physician or medical technician injecting the HA compositions. Although certain extrusion forces may be achievable with the HA compositions of the present description, one skilled in the art understands that high extrusion forces can lead to lack of control during injection and that such lack of control may result in additional pain to the patient. Extrusion forces of the present HA compositions can be from about 8 N to about 40 N, or more preferably from about 10 N to about 30 N, or about 15 N to about 20 N.

Sterilization, as used herein comprises any method known in the art to effectively kill or eliminate transmissible agents, preferably without substantially altering or degrading the HA-based compositions and any active agents.

One preferable method of sterilization of the filled syringes is by autoclave. Autoclaving can be accomplished by applying a mixture of heat, pressure and moisture to a sample in need of sterilization. Many different sterilization temperatures, pressures and cycle times can be used for this step. For example, the filled syringes may be sterilized at a temperature of at least about 120° C. to about 130° C. or greater. Moisture may or may not be utilized. The pressure applied is in some embodiments depending on the temperature used in the sterilization process. The sterilization cycle may be at least about 1 minute to about 20 minutes or more.

Another method of sterilization incorporates the use of a gaseous species which is known to kill or eliminate transmissible agents. Preferably, ethylene oxide is used as the sterilization gas and is known in the art to be useful in sterilizing medical devices and products.

A further method of sterilization incorporates the use of an irradiation source which is known in the art to kill or eliminate transmissible agents. A beam of irradiation is targeted at the syringe containing the HA solution, and the wavelength of energy kills or eliminates the unwanted transmissible agents. Preferable energy useful include, but is not limited to ultraviolet light, gamma irradiation, visible light, microwaves, or any other wavelength or band of wavelengths which kills or eliminates the unwanted transmissible agents, preferably without substantially altering of degrading the HA-based composition or any active agent.

EXAMPLE 1

EDC-Mediated Cross-Linked Polysaccharide

Polysaccharide hydrogels were generated by cross-linking HA using EDC and NHS (or sulfo-NHS, collectively "NHS").

Carbodiimide-mediated coupling of HA is performed in 0.1 M PBS at neutral pH (6.5-7.5). HA is dissolved in buffer (20-80 mg/mL). 5-30 mol % EDC and NHS are then added in one portion. Next, the polymer is allowed to cross-link over 12-72 hours at 22-60° C. The resulting gel may be diluted and is then dialyzed extensively at ambient temperature against PBS to remove N-acylurea byproducts and any unused starting materials. Sizing of the purified gel is then performed through a stainless steel screen.

EXAMPLE 2

EDC-Mediated Cross-Linked Polysaccharide-Protein

Polysaccharide-protein hydrogels were generated by cross-linking HA and elastin using EDC and NHS.

Carbodiimide-mediated coupling of HA and proteins (e.g. elastin) is performed in 0.1 M PBS at neutral pH (6.5-7.5). HA (20-80 mg/mL) and soluble elastin (2-20 wt %) are dissolved in PBS. 5-30 mol % EDC and NHS are added in one portion. Next, the polysaccharide and protein are allowed to cross-link at ambient temperature over 12-48 hours at 22-60° C. The resultant gel is then dialyzed extensively at ambient temperature against PBS to remove the N-acylurea byproducts and starting materials. Sizing of the purified gel is then performed through a stainless steel screen.

EXAMPLE 3

Rheology of Cross-Linked HA and HA-Elastin

The flow characteristics of the hydrogels prepared according to Examples 1 and 2 were evaluated in order to assess their elasticity and viscosity.

A strain sweep analysis provides information about a gel's elastic modulus (G') and viscous modulus (G"). A large value of G' compared to G" indicates a very elastic gel. FIG. 1 depicts typical strain sweep data for a hydrogel comprised of EDC/NHS cross-linked HA and HA-elastin. The G' for the two gels is 1100 Pa and 505 Pa, respectively where as that of BDDE crosslinked HA is 150 Pa. The G'/G" of the EDC/NHS cross-linked HA is 6.9 and that of HA-elastin is 3.7, respectively. In comparison, the G'/G" of BDDE-crosslinked HA is approximately 2.5. Taken together, these data suggest that the resulting gels from EDC/NHS mediated cross-linking have higher elasticity and hardness compared to BDDE-crosslinked hydrogel. Accordingly, EDC/NHS cross-linked HA and HA-proteins have improved properties suitable for soft tissue augmentation, such as, for example, dermal filling.

EXAMPLE 4

Enzyme Degradation of Cross-Linked HA and HA-Elastin

Hydrogels prepared according to Examples 1 and 2 were subjected to enzyme degradation in vitro to assess resistance to enzymatic degradation.

Figure 2:
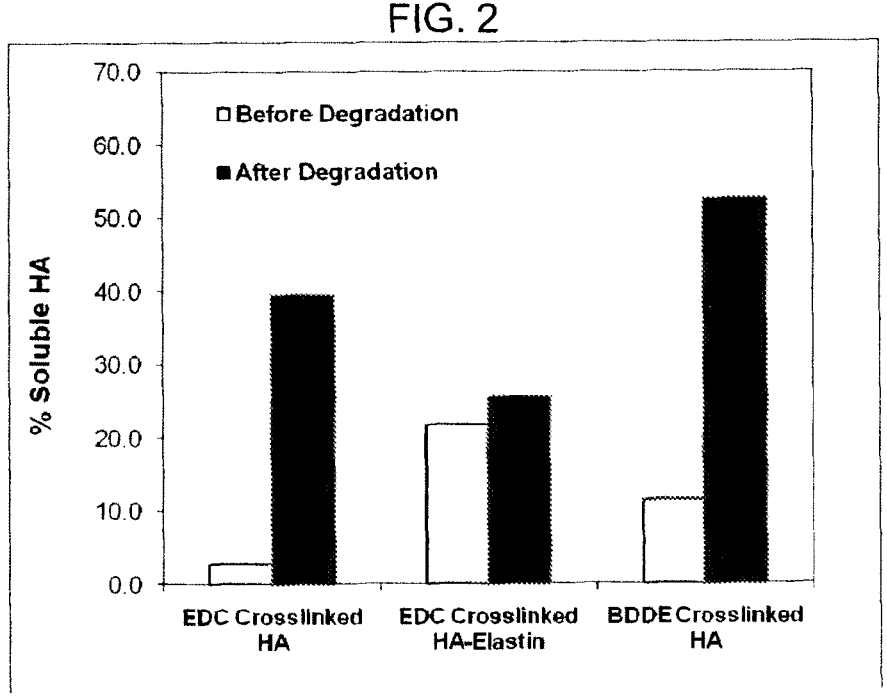
FIG. 2 graphically illustrates the resistance of HA and HA-elastin to enzyme degradation.

It is generally understood that improved resistance to enzyme degradation correlates to improved in vivo persistence. A superior gel resists degradation and therefore has a smaller difference of free HA before and after enzyme degradation. First, the percentage of uncross-linked (i.e., "free" HA) before and after enzymatic degradation with bovine testicular hyaluronidase (HAse) is measured by size exclusion chromatography (SEC) on an Agilent (Santa Clara, Calif.) HPLC system equipped with multi-angle laser light scattering (MALS) and refractive index detectors. FIG. 2 depicts enzymatic degradation of EDC/NHS cross-linked HA and HA-elastin, and BDDE-crosslinked HA hydrogel. As shown in FIG. 2, the increase in soluble HA is 37 and 4% for the EDC/NHS cross-linked HA and HA-elastin, respectively. The increase in soluble HA for BDDE crosslinked HA is 41%. Thus, HA-elastin resists enzymatic degradation more than the EDC/NHS cross-linked HA, and both HA and HA-elastin resist degradation more than BDDE crosslinked HA. As a result, EDC/NHS cross-linked HA and HA-proteins are expected to have improved in vivo persistence.

EXAMPLE 5

Extrusion of Cross-Linked HA and HA-Elastin

The extrusion force of hydrogels prepared according to Examples 1 and 2 were determined to evaluate the feasibility of administering the hydrogels through a needle.

Figure 3:
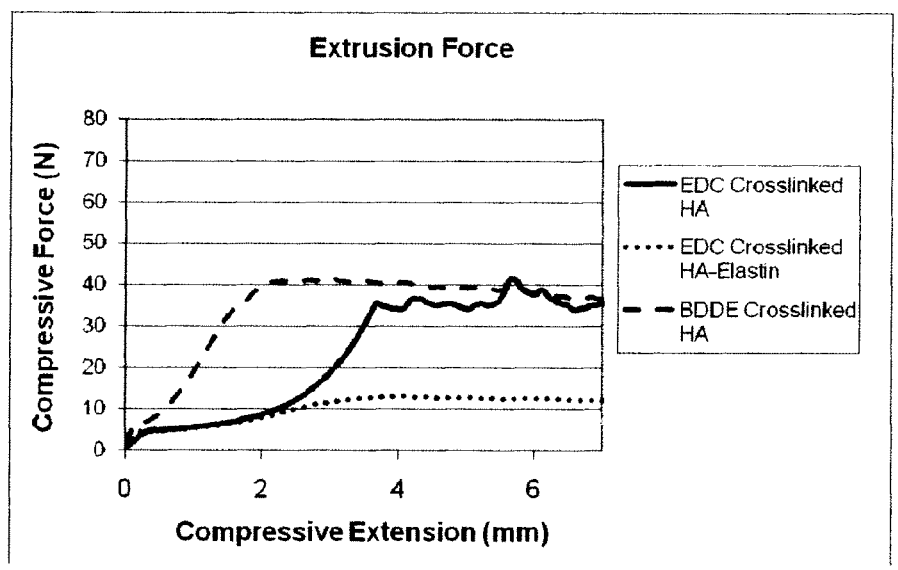
FIG. 3 graphically illustrates the extrusion force of EDC/NHS cross-linked HA and HA-elastin in accordance with an embodiment of the invention.

Extrusion force analysis was performed on an INSTRON® (Norwood, Mass.) instrument using a 0.8 mL syringe equipped with a 30 gauge (G) needle. The hydrogel was extruded at a constant rate of 50 mm/min. Shown in FIG. 3 is a graph of compressive extension plotted against compressive force for EDC/NHS cross-linked HA and HA-elastin as compared to BDDE crosslinked HA. These data show that the maximum average compressive force of the EDC/NHS cross-linked HA and HA elastin are 37 N and 13 N, respectively, while that of BDDE crosslinked HA is 38 N. Accordingly, EDC/NHS cross-linked HA and HA-elastin can be administered via injection through a 30 G needle.

EXAMPLE 6

Total Uncross-Linked HA

Total uncross-linked HA (i.e., free HA) was determined in the hydrogels prepared according to Examples 1 and 2.

The percentage of uncross-linked HA is an important parameter in evaluating relative cross-linking efficiency, as well as to predict the in vivo persistence of a hydrogel. It is well documented that uncross-linked HA is rapidly degraded in vivo; therefore, hydrogels with a larger percentage of uncross-linked HA are likely to have less in vivo persistence. Total uncross-linked HA is measured by diluting the gel 20× in PBS, and then allowing the gel to swell over 1 week with constant agitation. The solution is then filtered through a 0.22 µm filter to remove particulate and gel matter, and is then analyzed by SEC-MALS to measure the percentage of recovered HA. In this specific example, the EDC/NHS cross-linked HA and HA-elastin contain approximately 10% and 41% total uncross-linked HA, respectively. These data indicate that both EDC/NHS cross-linked HA and HA-elastin are expected to have suitable in vivo persistence.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although the invention has been described and illustrated with a certain degree of particularity, it is to be understood that the present disclosure has been made only by way of example, and that numerous changes in the combination and arrangement of parts can be resorted to by those skilled in the art without departing from the scope of the invention, as hereinafter claimed

What is claimed is:

1. A method for making a hydrogel for soft tissue augmentation, the method comprising:
   providing at least one cross-linkable biocompatible polymer;
   dissolving said at least one cross-linkable biocompatible polymer in a buffered solution, wherein said buffered solution maintains a pH from approximately 6.0 to approximately 8.0;
   adding at least one zero-length cross-linking agent to said buffered solution to form a reaction mixture; and
   allowing said reaction mixture to stand for a time appropriate to form the hydrogel suitable for soft tissue augmentation, wherein said hydrogel comprises a cross-linked biocompatible polymer having zero-length cross-linked moieties;
   wherein at least one said cross-linkable biocompatible polymer is hyaluronic acid; and
   wherein said zero-length cross-linking agent is 1-ethyl-3-(3-dimethylaminopropyl) carbodiimide (EDC).

2. The method according to claim 1 further wherein said buffered solution is phosphate buffered saline having a pH of between 6.5 and 7.5.

3. The method according to claim 1 further including N-hydroxysuccinimide (NHS) in said adding step.

4. The method according to claim 1 further comprising a dialyzing step after said allowing step.

5. The method according to claim 1 further comprising at least one second cross-linkable biocompatible polymer.

6. The method according to claim 5 wherein said at least one second cross-linkable biocompatible polymer is a protein.

7. The method according to claim 6 wherein said at least one second cross-linkable protein is elastin.

8. The method according to claim 1 further comprising adding an active agent selected from the group consisting of enzyme inhibitors, anesthetic agents, medicinal neurotoxins, antioxidants, anti-infective agents, anti-inflammatory agents, ultraviolet (UV) light blocking agents, dyes, hormones, immunosuppressants, and combinations thereof.

9. A method of making a hydrogel for soft tissue augmentation, the method comprising:
   reacting at least one cross-linkable biocompatible polymer with at least one zero-length cross-linking agent at neutral pH, thereby forming a cross-linked biocompatible polymer comprising zero-length cross-linked moieties;
   wherein at least one said cross-linkable biocompatible polymer is hyaluronic acid (HA); and
   wherein the zero-length cross-linking agent is 1-ethyl-3-(3-dimethylaminopropyl) carbodiimide (EDC).

10. The method according to claim 9, wherein the zero-length crosslinking agent is reacted with the at least one cross-linkable biocompatible polymer in the presence of N-hydroxysuccinimide (NHS).

11. The method according to claim 9, wherein the neutral pH is between about 6.0 and about 8.0.

12. The method according to claim 9, wherein the neutral pH is between about 6.5 and about 7.5.

13. The method according to claim 9, wherein the neutral pH is about 7.0.

14. The method according to claim 9, wherein the neutral pH is maintained by a phosphate buffered saline solution.

15. The method according to claim 9, further comprising at least one second cross-linkable biocompatible polymer.

16. The method according to claim 15, wherein the at least one second cross-linkable biocompatible polymer is a protein.

17. The method according to claim 16, wherein the at least one second cross-linkable protein is elastin.

18. The method according to claim 9, further comprising adding an active agent selected from the group consisting of enzyme inhibitors, anesthetic agents, medicinal neurotoxins, antioxidants, anti-infective agents, anti-inflammatory agents, ultraviolet (UV) light blocking agents, dyes, hormones, immunosuppressants, and combinations thereof.

19. The method according to claim 18, wherein the active agent is an anesthetic agent, which is lidocaine.

* * * * *